United States Patent [19]
Frazee et al.

[11] Patent Number: 5,665,753
[45] Date of Patent: Sep. 9, 1997

[54] CYTOKINE INHIBITING IMIDAZOLE SUBSTITUTED HYDROXAMIC ACID DERIVATIVES

[75] Inventors: James Simpson Frazee, Sewell, N.J.; John Gerald Gleason, Downingtown; Brian Walter Metcalf, Radnor, both of Pa.

[73] Assignee: SmithKline Beecham Corporation, Philadelphia, Pa.

[21] Appl. No.: 702,528

[22] PCT Filed: Mar. 3, 1995

[86] PCT No.: PCT/US95/02606

§ 371 Date: Sep. 3, 1996

§ 102(e) Date: Sep. 3, 1996

[87] PCT Pub. No.: WO95/23790

PCT Pub. Date: Sep. 8, 1995

[30] Foreign Application Priority Data

Mar. 3, 1994 [GB] United Kingdom .................. 9404046

[51] Int. Cl.⁶ .................... A01N 43/52; A61K 31/415; C07D 233/64; C07D 235/04

[52] U.S. Cl. .................... 514/394; 514/396; 548/302.7; 548/304.4; 548/335.1; 548/338.1; 548/343.5

[58] Field of Search .................... 514/394, 396; 548/302.7, 304.4, 335.1, 338.1, 343.5

[56] References Cited

U.S. PATENT DOCUMENTS

| | | | |
|---|---|---|---|
| 4,996,358 | 2/1991 | Handa et al. | 562/621 |
| 5,240,958 | 8/1993 | Campion et al. | 514/445 |
| 5,300,674 | 4/1994 | Crimmin et al. | 560/42 |
| 5,304,604 | 4/1994 | Davidson et al. | 514/238.2 |

*Primary Examiner*—Johann Richter
*Assistant Examiner*—Jane C. Oswecki
*Attorney, Agent, or Firm*—Dara L. Dinner; Stephen Venetianer; Edward T. Lentz

[57] ABSTRACT

The present invention relates to a series of novel imidazole substituted hydroxamic acid derivatives, and compositions useful thereof as inhibitors of matrix degrading metalloproteinases, in particular collagenase.

16 Claims, No Drawings

CYTOKINE INHIBITING IMIDAZOLE SUBSTITUTED HYDROXAMIC ACID DERIVATIVES

FIELD OF THE INVENTION

This invention relates to novel compounds for both pharmaceutical and veterinary treatment of matrix-degrading metalloproteinase related disease states.

BACKGROUND OF THE INVENTION

Many different metalloproteinase enzymes are involved in connective tissue degradation or breakdown, such as collagenase, stromelysin and gelatinase. Inhibitors of matrix degrading metalloproteinases (MMP's) are known to be useful in the treatment or prophylaxis of conditions involving such tissue degradation. Such diseases include rheumatoid arthritis, osteoarthritis, arthropathy, dermatological conditions, bone resorption, inflammatory diseases, tumor invasion or metastasis, in the promotion of wound healing, osteoporosis, rheumatoid arthritis, periodonititis, gingivitis, and corneal ulceration, gastric ulceration.

A number of hydroxamic acid derivatives have been suggested as being useful as collagenase inhibitors, or for promoting tumor regression, such as those in the following patents and patent applications: U.S. Pat. No. 4,599,361; EP 236872; WO 90/05716; WO 91/02716; WO 90/05719; WO 93/20047; EPO 0 498 665 A1; and WO 93/21942.

These compounds, however, have generally poor pharmacokinetic properties and or poor water solubility. Therefor a need still exists to identify novel compounds which overcome these deficiencies.

SUMMARY OF THE INVENTION

The present invention relates to a series of novel imidazole substituted hydroxamic acid derivatives, and compositions useful thereof as inhibitors of matrix-degrading metalloproteinase. By inhibiting the action of metalloproteinases the compounds of Formula (I) may be used in the treatment of disease states mediated thereby.

This invention relates to the novel compounds of Formula (I) and pharmaceutical compositions comprising a compound of Formula (I) and a pharmaceutically acceptable diluent or carrier.

This invention also relates to a method of inhibiting cytokines and the treatment of a cytokine mediated disease, in a mammal in need thereof, which comprises administering to said mammal an effective amount of a compound of Formula (I).

Compounds of Formula (I) have the following structure:

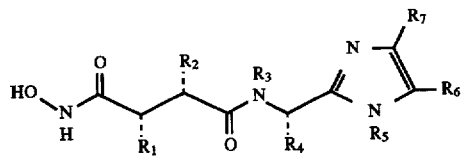

(I)

wherein $R_1$ is hydrogen, hydroxy, optionally substituted $C_{1-6}$ alkyl, optionally substituted $C_{1-6}$ alkenyl, phenyl, optionally substituted phenyl $C_{1-6}$ alkyl-, $R_7$—$S(O)_n C_{1-6}$-alkyl-;

n is 0 or an integer having a value of 1 or 2;

$R_7$ is $C_{1-6}$ alkyl, phenyl, phenyl $C_{1-6}$ alkyl, heterocyclic, heterocyclic $C_{1-6}$ alkyl, heteroaryl, heteroaryl $C_{1-6}$ alkyl, $C_{1-6}$ alkyl carbonyl, or phenacyl, all of which may be optionally substituted one to four time independently from C1–6 alkyl, $C_{1-6}$ alkoxy, hydroxy, thio $C_{1-6}$alkyl, amino, halogen, $CF_3$ or nitro;

$R_2$ is hydrogen, $C_{1-6}$alkyl, $C_{1-6}$ alkenyl, phenyl $C_{1-6}$ alkyl, cycloalkyl $C_{1-6}$ alkyl, or cycloalkenyl $C_{1-6}$ alkyl;

$R_3$ is hydrogen or methyl;

$R_4$ is hydrogen, $C_{1-6}$ alkyl, cyclopropyl, an amino acid residue, optionally substituted phenyl, optionally substituted phenyl $C_{1-6}$ alkyl-, optionally substituted —$C_{1-6}$-alkyl-oxy $C_{1-6}$alkyl, optionally substituted —$C_{1-6}$ alkyl oxy $C_{1-6}$ alkyl phenyl, or an optionally substituted —$C_{1-6}$ alkyl oxy phenyl;

wherein the phenyl or benzyl moiety is independently substituted one to four times by halogen, $C_{1-6}$ alkyl, $C_{1-6}$ alkoxy, hydroxy, thiol, $C_{1-6}$alkylthio-, —$NR_{12}R_{13}$, —$NHR^a$, —$NO_2$, —$C(O)_2R_{14}$, —$C(O)_2NR_{12}R_{13}$, cyanoamino, $R_{14}C(O)$—$O$—, $C_{1-6}$ alkyl OH, $C_{1-6}$ alkyl-$C(O)_2R_{14}$, $C_{1-6}$ alkyl-oxy-$C_{1-6}$ alkyl, $C(O)C_{1-6}$ alkylNR$_{12}$R$_{13}$, or $C_{1-6}$ alkyl-(O)$_2$C—R$_{14}$;

$R^a$ is hydrogen, $C_{1-6}$ alkyl, or the side chain of an amino acid, $R_{14}$ is hydrogen, $C_{1-6}$ alkyl, $C_{3-7}$ cycloalkyl, $C_{3-7}$ cycloalkyl $C_{1-6}$ alkyl, aryl $C_{1-6}$ alkyl, heteroaryl$C_{1-6}$alkyl, or heterocyclic $C_{1-6}$ alkyl;

$R_5$ is hydrogen or $C_{1-6}$ alkyl;

$R_6$ and $R_7$ are independently hydrogen, halogen, $CF_3$, $C_{1-6}$ alkyl, aryl, aryl$C_{1-6}$alkyl, heteroaryl, heteroaryl $C_{1-6}$ alkyl, heterocyclic, heterocyclic $C_{1-6}$ alkyl, $(CHR_8)m'$ OH, $(CHR_8)m$ $C(O)_2R_{10}$, $(CHR_8)m$ $C(OH)(R_9)_2$, $(CR_8R_9)$—OH, $C(O)R_{11}$, $C(O)NR_{12}R_{13}$, $C(O)_2R_{10}$, or $NO_2$; or $R_6$ and $R_7$ can together form a fused C 2–4 alkylene, aryl or heteroaryl moiety;

m is 0 or an integer having a value of 1 or 2;

m' is an integer having a value of 1, 2, or 3;

$R_8$ and $R_9$ are independently hydrogen, $C_{1-4}$ alkyl or phenyl;

$R_{10}$ is hydrogen, $C_{1-6}$ alkyl, $C_{3-7}$ cycloalkyl, $C_{3-7}$ cycloalkyl $C_1$_alkyl, $C_{5-7}$ cycloalkenyl, aryl$C_{1-6}$alkyl, heteroaryl$C_{1-6}$alkyl, heterocyclic, heterocyclic $C_{1-6}$ alkyl all of which may be optionally substituted by halogen, hydroxyl, —$C_{1-6}$alkoxy, -thio$C_{1-6}$ alkyl, or $CF_3$;

$R_{11}$ is hydrogen, $C_{1-6}$ alkyl, $C_{3-7}$ cycloalkyl, $C_{3-7}$ cycloalkyl $C_{1-6}$ alkyl, $C_{5-7}$ cycloalkenyl, aryl, aryl$C_{1-6}$alkyl, heteroaryl, heteroaryl$C_{1-6}$ alkyl, heterocyclic, heterocyclic $C_{1-6}$ alkyl all of which may be optionally substituted by halogen, hydroxyl, —$C_{1-6}$ alkoxy, -thio$C_{1-6}$ alkyl, or $CF_3$;

$R_{12}$ and $R_{13}$ are independently hydrogen, $C_{1-6}$ alkyl, $C_{3-7}$ cycloalkyl, $C_{3-7}$ cycloalkyl $C_{1-6}$ alkyl, aryl, aryl$C_{1-6}$ alkyl, heteroaryl, heteroaryl $C_{1-6}$ alkyl, heterocyclic, heterocyclic $C_{1-6}$ alkyl or $R_{12}$ and $R_{13}$ may together with the nitrogen to which they are attached form a 5 to 7 membered ring which may additionally contain another heteroatom selected from O/N/or S;

or a pharmaceutically acceptable salt thereof.

DETAILED DESCRIPTION OF THE INVENTION

The compounds of the present invention may contain one or more asymmetric carbon atoms and may exist in racemic and optically active forms. All of these compounds, specifically racemic mixtures and stereoisomers thereof are included within the scope of the present invention.

Compounds of Formula (I) have the preferred chiral structure shown below and, illustrated herein with $R_2$ as isobutyl.

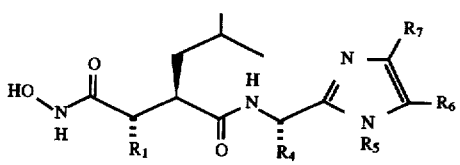

Additionally, compounds in which the chiral centre adjacent to the substituent $R_4$ has the S steriochemistry and/or the chiral centre adjacent to the substituent $R_2$ which has an R steriochemistry are preferred.

Suitably, $R_1$ is hydrogen, hydroxy, or phenyl, benzyl, or $R_7$—S(O)$_n$ $C_{1-6}$ alkyl- wherein the $C_{1-6}$ alkyl is preferably methylene. $R_7$ is preferably phenyl and n is 0.

Suitably, $R_2$ is $C_{1-6}$ alkyl, more preferably isobutyl.

Suitably, $R_3$ is hydrogen or methyl, preferably hydrogen.

Suitably, $R_4$ is hydrogen, $C_{1-6}$ alkyl, cyclopropyl, an amino acid residue, optionally substituted phenyl, optionally substituted phenyl $C_{1-6}$ alkyl-, optionally substituted —$C_{1-6}$-alkyl-oxy $C_{1-6}$alkyl, optionally substituted —$C_{1-6}$ alkyl oxy$C_{1-6}$ alkyl phenyl, or an optionally substituted —$C_{1-6}$ alkyl oxy phenyl; wherein the phenyl or benzyl moiety is independently substituted one to four times by halogen, $C_{1-6}$ alkyl, $C_{1-6}$ alkoxy, hydroxy, thiol, $C_{1-6}$alkylthio-, —$NR_{12}R_{13}$, —$NHR^a$, —$NO_2$, —$C(O)_2R_{14}$, —$C(O)_2NR_{12}R_{13}$, cyanoamino, $R_{14}C(O)$—O—, $C_{1-6}$ alkyl OH, $C_{1-6}$ alkyl-$C(O)_2R_{14}$, $C_{1-6}$alkyl-oxy-$C_{1-6}$alkyl, C(O) $C_{1-6}$ alkylN$R_{12}R_{13}$, or $C_{1-6}$ alkyl-(O)$_2$C—$R_{14}$.

Suitably, $R_6$ and $R_7$ are independently hydrogen, bromine, chlorine, $CF_3$, $C_{1-6}$ alkyl, phenyl, (CHR$_8$)m' OH, (CHR$_8$)m $C(O)_2R_{10}$, (CHR$_8$)m $C(OH)(R_9)_2$, ($CR_8R_9$)—OH, $C(O)R_{11}$, $C(O)NR_{12}R_{13}$, $C(O)_2R_{10}$, or $NO_2$; or $R_6$ and $R_7$ can together form a fused C2–4 alkylene, aryl or heteroaryl moiety. Preferably the fused ring forms an (i.e., aryl) ting to result in a benzoimidazole moiety.

Preferably, when $R_{10}$ is hydrogen, or $C_{1-6}$ alkyl, preferably the alkyl is methyl or isopropyl.

Suitably, $R_{11}$ is hydrogen, $C_{1-6}$ alkyl, or phenyl, preferably the alkyl is methyl or isopropyl.

When either $R_6$ or $R_7$ is (CHR$_8$)m $C(O)_2R_{10}$ than m is preferably 0 or 2.

When either $R_6$ or $R_7$ is (CHR$_8$)m OH than $R_8$ is preferably hydrogen, methyl, isopropyl, or phenyl.

Preferably, in a preferred grouping, $R_1$ is hydrogen or hydroxy; $R_2$ is $C_{1-6}$ alkyl, more preferably isobutyl, $R_3$ is hydrogen; $R_4$ is hydrogen, methyl, t-butyl, ethyl, propyl, isobutyl, cyclopropyl or benzyl, preferably $C_{1-6}$ alkyl, more preferably isopropyl; $R_6$ and $R_7$ are hydrogen, $C_{1-6}$ alkyl, $C_{3-6}$ cycloalkyl, phenyl, benzyl, $CF_3$, bromine, $C(O)_2CH_3$, $C(H)O$, $CH_2OH$, $CH(OH)CH_3$, $CH(OH)$isopropyl, $CH(OH)$ phenyl, $NO_2$, $C(O)NH_2$, $(CH_2)_2C(O)CH_3$, or both of $R_6$ and $R_7$ are methyl, dibromo or together form a fused aryl ring with the imidazole.

In a preferred embodiment the compounds of Formula (I) are those wherein $R_1$ is hydrogen, or hydroxy;

$R_2$ is $C_{1-6}$alkyl;

$R_3$ is hydrogen;

$R_4$ is hydrogen, $C_{1-6}$ alkyl, cyclopropyl, an amino acid residue, optionally substituted phenyl, optionally substituted phenyl $C_{1-6}$ alkyl-, optionally substituted —$C_{1-6}$-alkyl-oxy $C_{1-6}$ alkyl, optionally substituted —$C_{1-6}$ alkyl oxy$C_{1-6}$ alkyl phenyl, an optionally substituted —$C_{1-6}$ alkyl oxy phenyl, or phenyl-$C_{1-6}$ alkyl-oxy $C_{1-6}$ alkyl;

wherein the phenyl or benzyl moiety is independently substituted one to four times by halogen, $C_{1-6}$ alkyl, $C_{1-6}$ alkoxy, hydroxy, thiol, $C_{1-6}$alkylthio-, —$NR_{12}R_{13}$, —$NHR^a$, —$NO_2$, —$C(O)_2R_{14}$, —$C(O)_2NR_{12}R_{13}$, cyanoamino, $R_{14}C(O)$—O—, $C_{1-6}$ alkyl OH, $C_{1-6}$alkyl-$C(O)_2R_{14}$, $C_{1-6}$ alkyl-oxy-$C_{1-6}$alkyl, $C(O)C_{1-6}$ alkylN$R_{12}R_{13}$, or $C_{1-6}$alkyl-$(O)_2C$-$R_{14}$ $R_5$ is hydrogen or methyl, $C_{1-6}$ alkyl;

$R_6$ and $R_7$ are independently hydrogen, bromine, chlorine, $CF_3$, $C_{1-6}$ alkyl, phenyl, (CHR$_8$)m' OH, (CHR$_8$)m $C(O)_2R_{10}$, (CHR$_8$)m $C(OH)(R_9)_2$, ($CR_8R_9$)—OH, $C(O)R_{11}$, $C(O)NR_{12}R_{13}$, $C(O)_2R_{10}$, or $NO_2$; or $R_6$ and $R_7$ can together form a fused C2–4 alkylene, aryl or heteroaryl moiety;

m is an integer having a value of 1, 2, or 3;

m' is 0 or an integer having a value of 1 or 2;

$R_8$ and $R_9$ are independently hydrogen, $C_{1-4}$ alkyl, or phenyl;

$R_{10}$ is hydrogen, or $C_{1-6}$ alkyl;

$R_{11}$ is hydrogen, $C_{1-6}$ alkyl, or phenyl;

$R_{12}$ and $R_{13}$ are independently hydrogen, $C_{1-6}$ alkyl, $C_{3-7}$ cycloalkyl, $C_{3-7}$ cycloalkyl $C_{1-6}$ alkyl, aryl, aryl$C_{1-6}$ alkyl, heteroaryl, heteroaryl$C_{1-6}$ alkyl, heterocyclic, heterocyclic $C_{1-6}$ alkyl or $R_{12}$ and $R_{13}$ may together with the nitrogen to which they are attached form a 5 to 7 membered ring which may additionally contain another heteroatom selected from O/N/or S;

or a pharmaceutically acceptable salt thereof.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of formula (I) may also be formed with a pharmaceutically acceptable cation, for instance, if a substituent $Y_1$ in $R_3$ comprises a carboxy group. Suitable pharmaceutically acceptable cations are well known to those skilled in the art and include alkaline, alkaline earth, ammonium and quaternary ammonium cations.

Another aspect of the present invention is a pharmaceutical composition comprising a pharmaceutically acceptable carrier or diluent and a compound according to Formula (I).

The following terms, as used herein, refer to:

"halo"—all halogens, that is chloro, fluoro, bromo and iodo;

"alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, and the like;

The term "cycloalcyl" is used herein to mean cyclic radicals, preferably of 3 to 7 carbons, including but not limited to cyclopropyl, cyclopentyl, cyclohexyl, and the like.

The term "cycloalkenyl" is used herein to mean cyclic radicals, preferably of 5 to 7 carbons, which contains an unsaturated bond, including but not limited to cyclopentenyl, cyclohexenyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl"(on its own or in any combination, such as "heteroaryloxy")—a 5–10 membered aromatic ring system in which one or more rings contain one or more heteroatoms selected from the group consisting of N, 0 or S, such as, but not limited, to pyrrole, thiophene, quinoline, isoquinoline, pyridine, pyrimidine, oxazole, thiazole, thiadiazole, triazole, imidazole, or benzimidazole;

"heterocyclic"(on its own or in any combination, such as "heterocyclylalkyl") —a saturated or wholly or partially unsaturated 4–10 membered ring system in which one or more rings contain one or more heteroatoms selected from the group consisting of N, O, or S; such as, but not limited to, pyrrolidine, piperidine, piperazine, morpholine, imidazolidine or pyrazolidine;

The term "aralkyl" or "heteroarylalkyl" or "heterocyclIcalkyl" is used herein to mean $C_{1-6}$ alkyl as defined above unless otherwise indicated.

The term "amino acid residue" is used herein to mean a characteristic side chain attached to the —CH(NH$_2$)COOH moiety in the following R or S amino acids, glycine, phenyl glycine, alanine, valine, leucine, isoleucine, phenylalanine, tyrosine, tryptophan, serine, threonine, cysteine, methionine, asparagine, glutmine, lysine, histidine, arginine, glutamic acid and aspartic acid.

Compounds of Formula (I) are imidazole derivatives which may be readily prepared using procedures well known to those of skill in the art such as may be found in U.S. Pat. No. 4,599,361; EP 236872; WO 90/05716; WO 91/02716; WO 90/05719; WO 93/20047; EPO 0 498 665 A1; and WO 93/21942 whose disclosures are hereby incorporated by reference, or may be prepared by analogous methods to those indicated herein below.

Scheme I

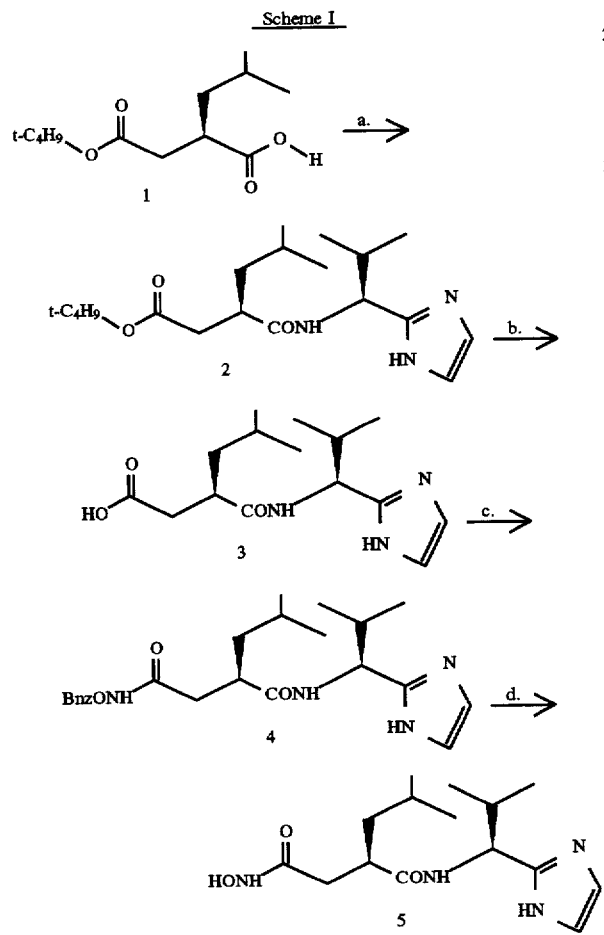

a) (1S)-1-amino-1-isopropyl-1-(imidazo-2-yl)methane, benzotriazol-1-yloxy-tris(dimethylamino)phosphonium hexafluorophosphate ("BOP" rgt.), Et$_3$N, CH$_2$Cl$_2$; b) CF$_3$COOH; c) H$_2$NOCH$_2$Ph·HCl, "BOP" rgt., Et$_3$N, CH$_2$Cl$_2$; d) H$_2$, Pd/C, EtOH.

While the instant scheme, and scheme 2 to 4 as well are shown with a particular compound according to formula (I), here (in scheme 1) $R_1$ is hydrogen, $R_2$ is iso-butyl, $R_3$ is hydrogen, $R_4$ is isopropyl, $R_5$, $R_6$ and $R_7$ are hydrogen, the methods noted herein may be extrapolated to include all compounds of Formula (I) accordingly.

Monoesters of a dicarboxylic acid such as 1-Scheme-1 may be prepared according to procedures found in European Pat App. 0 498 665-A1, in particular see Example 1C, page 11 thereof. 1-Scheme-1 is coupled with a suitable amine (a), in this case a substituted aminomethyl imidazole which is available from any α-amino acid as in Scheme 3. The coupling is carried out using any standard coupling agent used in peptide synthesis, in this case "BOP" reagent to give 2-Scheme-1, in an organic solvent, such as but not limited to halogenated hydrocarbons, tetrahydrofuran, ethyl acetate, toluene, benzene, acetone, ethers, acetonitrile and DMF. The ester group in 2-Scheme-1 is deprotected using standard reagents, in this case trifluoroacetic acid as its own solvent of TFA in chloroform or TFA in methylene chloride. The carboxylic acid 3-Scheme-1, is coupled with a suitably protected hydroxylamine, in this case O-benzylhydroxylamine, using "BOP" reagent as the coupling agent in solvents such as water, aqueous hydrochloric acid, acetic acid, ethyl acetate, the various alcohols, such as ethanol, methanol or isopropanol. The protecting group on the hydroxamic acid 4-Scheme-1 is removed using standard conditions, in this case catalytic hydrogenation over a palladium catalyst, and gave the final product 5-Scheme-1.

Scheme 2

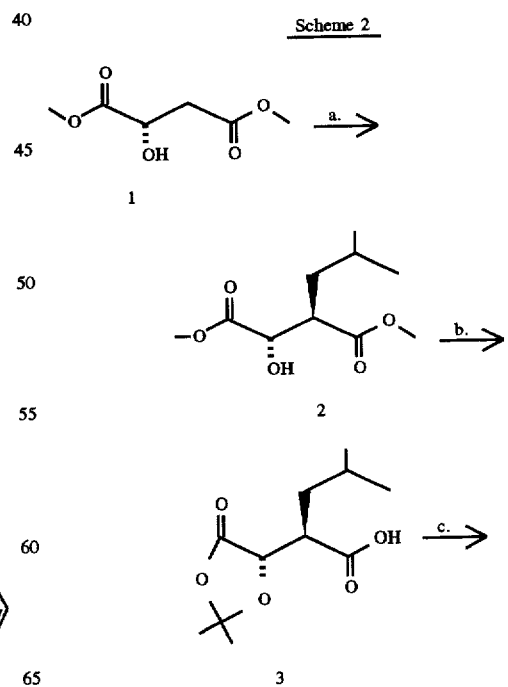

-continued
Scheme 2

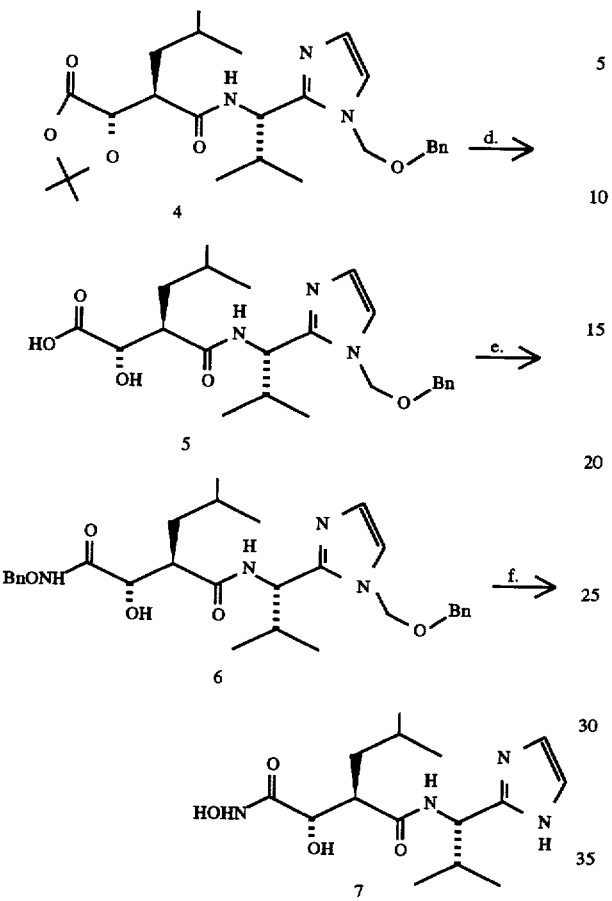

a) 2 LiN(i-propyl)$_2$, i-butylbromide; b) (1) NaOH (2) Me$_2$C(OMe)$_2$, p-TSA; c) (1) pentafluorophenol, WSDI (2) substituted aminomethyl imidazole, DMF; d) HCl, H$_2$O, ethylene glycol; e) BnONH$_2$·HCl, Et$_3$N, WSDI; f) H$_2$, Pd/C The diester of malic acid, commercially available, 1-Scheme-2 can be alkylated according to the procedure of Seebach et aL, *Helv. Chim. Acta*, 1980, 63, 197. In this case the dianion of the diester is alkylated with i-butyl bromide to give 2-Scheme-2, wherein R$_2$ is isobutyl and R$_1$ is hydroxyl, under reaction conditions wherein the solvents such as THF, ether, or dimethoxy ethane are suitably used, and a primary or secondary bromide derivative of R$_2$ may be used. The esters can be cleaved under standard hydrolytic conditions, in this case with aqueous NaOH, (or NaOH in aq. alcohols or aq. THF) and the α-hydroxy carboxylic acid can be protected as the acetonide, in this case by reaction of the hydroxy acid with dimethoxypropane under acid catalysis, in this case using p-toluenesulfonic acid. 3-Scheme-2 is first coupled with pentafluorophenol using a standard coupling agent, in this case a water soluble diimide (WSDI), specifically 1-ethyl-3-dimethylaminopropyl-carbodiimide methiodide in organic solvents such as the halogenated hydrocarbons, tetrahydrofuran, ethyl acetate, toluene, benzene, acetone, ethers, acetonitrile and DMF; and the resultant active ester is coupled with a suitably substituted aminomethyl imidazole obtained from the procedure of 4-Scheme-4 in solvents such as DMF or chlorinated hydrocarbons. In this instance, R$_3$ is hydrogen, R$_4$ is isopropyl, R$_6$ and R$_7$ are hydrogen, and R$_5$ as a hydrogen is suitably protected, this compound being derived from valine. The acetonide protecting group in 4-Scheme-2 can be removed under acidic conditions, in this case with aqueous HCl in ethylene glycol or any suitable alcohol. As noted in scheme 4 compounds wherein R$_3$ and/or R$_5$ is methyl can suitably be prepared. The free carboxylic acid in 5-Scheme-2 can be coupled under standard conditions with a suitably protected hydroxylamine, in this case O-benzyl-hydroxylamine, to give the protected hydroxamic acid 6-Scheme-2. Simultaneous deprotection of the hydroxamic acid and the imidazole can be accomplished using conditions appropriate to the protecting groups, in this case catalytic hydrogenation over a palladium catalyst to give the final product 7-Scheme-2.

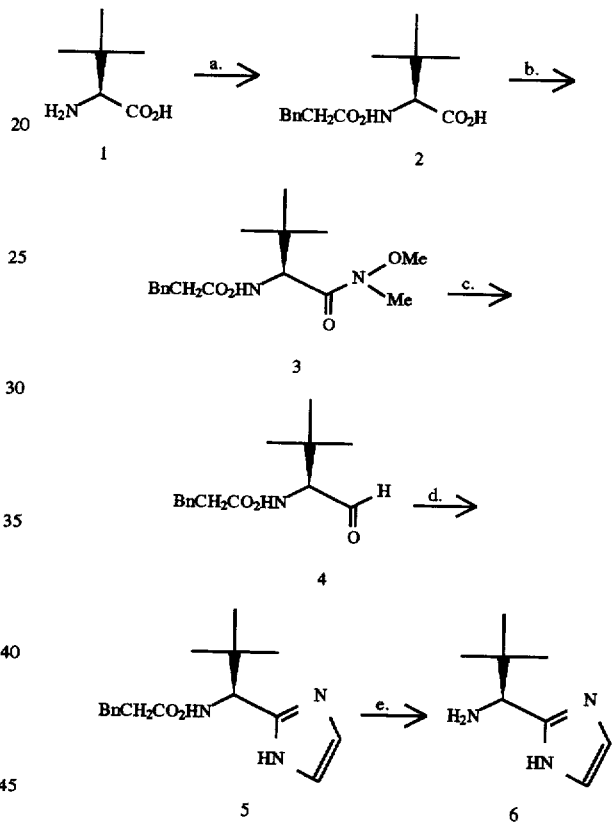

a) PhCH$_2$OCOCl, NaOH, aqueous Me$_2$CO; b) (1) pentafluorophenol, WSDI (2) HN(OMe)Me·HCl, Et$_3$N, DMF; c) LiAlH$_4$, −55°; d) NH$_3$, glyoxal tdmer, MeOH; e) H$_2$, Pd/C.

Any α-amino acid, including phenylglycine (which produces the final product of formula (I) wherein R4 is phenyl), but in this case tert-leucine is illustrated for R4 as a t-butyl group (tert-leucine is available from Aldrich Chemical Co.) which amino acid can have the nitrogen protected as a carbamate, in this case a carbobenzyloxy group, using standard conditions, such as in aq. THF, or alternatively this can be done under anhydrous condition such as triethylamine as a base and chlorinated solvents, to give 2-Scheme-3. Alternatively, amino acid derivatives of interest can be prepared in accordance with the procedures illustrated in WO93/02057, in particular, Example 1(a) whose disclosure is hereby incorporated by reference. The carboxyl group of 2-Scheme-3 is activated by formation of an active ester, in this case the pentafluorophenyl ester, the coupling between the carboxylic acid and the phenol being carried out with any water soluble diimide, in solvents such as halogenated hydrocarbons, tetrahydrofuran, ethyl acetate, toluene, benzene, acetone, ethers, acetonitrile and DMF, in this case the WSDI is 1-cyclohexyl-3-(2-morpholinoethyl)-carbodiimide metho-p-toluene-sulfonate. The active ester is coupled with N,O-dimethylhydroxylamine to give the amide 3-Scheme-3. The amide is reduced to the aldehyde, in this case using $LiAlH_4$ at reduced temperatures, in this case $-55°$, in solvents such as THF, ether, or dimethoxy ethane, to give the aldehyde of 4-Scheme-3. Condensation of the aldehyde with glyoxal and ammonia in any alcoholic solvent, gives the imidazole 5-Scheme-3, and the protecting group is removed using conditions appropriate for the particular protecting group, in this case catalytic hydrogenation over a palladium catalyst to give the substituted aminomethyl imidazole, 6-Scheme-3, used in scheme 1.

Appropriately substituted intermediates of 6-Scheme-3, for use in the present invention may be produced in accordance with the procedures found in WO 93/02057, supra, as follows:

| $R_4$ | $R_5$ | $R_6$ | $R_7$ | Exam. # |
|---|---|---|---|---|
| isopropyl | Hydrogen | Hydrogen | Hydrogen | 1(b) |
| isopropyl | Hydrogen | Hydrogen | $(CH_2)_2C(O)_2CH_3$ | 83(b) |
| isopropyl | Hydrogen | Hydrogen | $C(O)NH_2$ | 84(d) |
| isopropyl | Hydrogen | methyl | methyl | 9(b) |
| isopropyl | Hydrogen | Hydrogen | phenyl | 18(c) |
| isopropyl | Hydrogen | $R_6$ & R7 | forms fused aryl ring | 4(b) |
| isopropyl | Hydrogen | Hydrogen | bromine | 21(b) |
| isopropyl | Hydrogen | bromine | Bromine | 22(a) |
| isopropyl | Hydrogen | Hydrogen | methyl | 23(a) |
| isopropyl | Hydrogen | Hydrogen | $CF_3$ | 24(a) |
| isopropyl | Hydrogen | Hydrogen | $C(O)_2CH_3$ | 26(c) |
| isopropyl | Hydrogen | Hydrogen | $CH_2OH$ | 30(a) |
| isopropyl | Hydrogen | Hydrogen | CH(O) | 27(b) |
| isopropyl | Hydrogen | Hydrogen | $CH(OH)CH(CH_3)_2$ | 28(b) |
| isopropyl | Hydrogen | Hydrogen | CH(OH)phenyl | 29(b) |
| isopropyl | Hydrogen | Hydrogen | $CH(OH)CH_3$ | 27(d) |
| methyl* | Hydrogen | Hydrogen | Hydrogen | 6(a) |
| Hydrogen* | Hydrogen | Hydrogen | Hydrogen | 5(a) |
| $CH_2$-phenyl | Hydrogen | Hydrogen | Hydrogen | 7(a) |
| ethyl | Hydrogen | Hydrogen | Hydrogen | 19(b) |
| propyl | Hydrogen | Hydrogen | Hydrogen | 20(b) |
| isobutyl* | Hydrogen | Hydrogen | Hydrogen | 36(a) |
| cyclopropyl | Hydrogen | Hydrogen | Hydrogen | 61(d) |
| isopropyl$_a$ | methyl | Hydrogen | Hydrogen | 11(a) |
| isopropyl$^b$ | Hydrogen | Hydrogen | Hydrogen | 25(b) |

*is a protected site with a carbobenzyloxy moiety
$^a$is a protected carbobenzyloxy amino group
$^b R_3$ is methyl, i.e. the amino is group is $NHCH_3$ These intermediates can serve as precursers to other usefully substituted intermediates, such as where $R_7$ is $C(O)NH2$ could also be made thru the intermediate C(O) 2Me with appropriately subsituted $NR_{12}R_{13}$ moieties to yield the $R_7$ group–$C(O)NR_{12}R_{13}$.

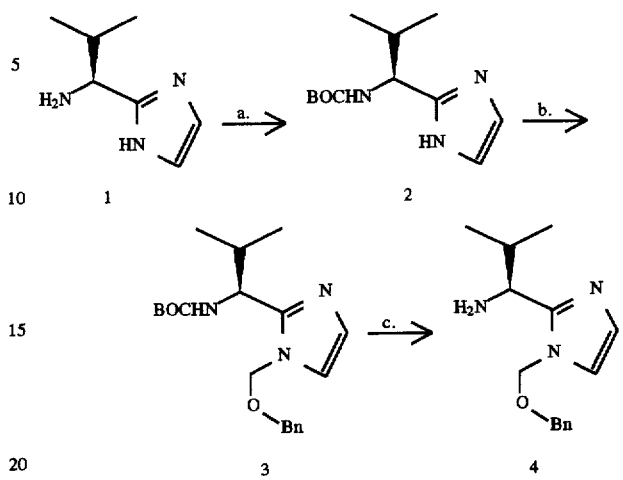

Scheme 4 a) (1) di-t-butylpyrocarbonate, MeOH (2) NaOH, aqueous MeOH; b) benzyl chloromethyl ether, $Et_3N$, MeCN; c) (1) $CF_3COOH$ (2) $K_2CO_3$.

A substituted aminomethyl imidazole, such as available from the procedures outlined in Scheme 3 herein, in this case (1S )-1-amino-1-isopropyl-1-(imidazo-2-yl)methane, 1 -Scheme-4, can have the amino group protected, in this case as the t-butoxycarbonyl group, by reaction with a suitable derivatizing agent, in this case di-t-butyl-pyrocarbonate in chlorinated solvents, or alcohols. The NH of the imidazole in compound 2-Scheme-4 can be blocked by alkylation, in this case alkylation is carried out under basic conditions with benzyl chloromethyl ether, and alternative solvents such as DMF or acetone, to give the doubly protected compound 3-Scheme-4. The protecting group on the primary amine is selectively removed, in this case with trifluoroacetic acid (neat or in chlorinated solvents), and the resulting trifluoroacetate salt of the amine is neutralized with a base to give the product 4-Scheme-4. Alternatively, prior to selectively deprotecting the side chain nitrogen, the hydrogen may be removed and replaced with a methyl group (for $R_3$) with NaH and MeI and the reaction scheme proceeds accordingly, or (for $R_5$ other than hydrogen) using the intermediate of 2-Scheme-4 and methyl iodide instead of benzylchloromethyl ether, and working up accordingly will produce suitably substituted compounds. Yet another method for $R_3$ as other than hydrogen, the intermediate of 5-Scheme-3 may be used as intermediates to make other $R_5$ alkyl groups. Alkylation of the compound 5-Scheme-3 would first alkylate on the imidazole ring, and the resulting compound would then be used as an intermediate for alkylation, by standard means of the side chain nitrogen so that both $R_3$ and $R_5$ would be appropriately substituted.

Suitable protecting groups for use herein are well known in the art and described in many references, for instance, Protecting Groups in Organic Synthesis, Greene T W, Wiley-Interscience, New York, 1981.

Pharmaceutically acid addition salts of compounds of formula (I) may be obtained in known manner, for example by treatment thereof with an appropriate amount of acid in the presence of a suitable solvent.

The invention will now be described by reference to the following examples which are merely illustrative and are not to be construed as a limitation of the scope of the present invention.

SYNTHETIC EXAMPLES

Example 1

N-Hydroxy-3-N'-(1'-isopropyl-1'-imidazol-2-yl) methylaminocarbonyl-5-methyl hexanamide Preparation of (3R, 1'S)-N-Hydroxy-3-(N'-(1'-isopropyl-1'-imidazol-2-yl)methylaminocarbonyl)-5-methyl hexanamide (wherein $R_1$=H, $R_4$=i-propyl)

a) (3R, 1'S)-t-butyl-3-(N'-(1'-isopropyl-1'-imidazol-2-yl) methylaminocarbonyl)-5-methyl hexanoate A solution of (3R)-t-butyl-3-i-butyl succinate (193 mg, 0.84 mmole), (1S)-1-(imidazol-2-yl)-2-methylpropylamine (117 mg, 0.84 mmole), $Et_3N$ (170 mg, 1.68 mmole) and benzotriazolo-1-yloxy-tris(dimethylamino)phosphonium hexafluorophosphate (372 mg, 0.84 mmole) in $CH_2Cl_2$ (10ml) was stirred for 18 hr. The reaction was diluted with $Et_2O$ (10 0ml), and washed with $H_2O$ and aq $Na_2CO_3$. The organic extracts were dried ($K_2CO_3$), and the solvent removed. The residue was recrystallized from a mixture of $CH_2Cl_2$ and hexane to afford the title compound (160 mg, 54%). $^1H$ NMR (400 MHz, $CDCl_3$) δ6.95 (s, 2H), 4.68 (t, 1H), 2.72 (m, 1H), 2.42 (m, 1H).

b) (3R, 1'S)-3-(N'-(1'-isopropyl-1'-imidazol-2-yl) methylaminocarbonyl)-5-methyl hexanoic acid, trifluoroacetate salt A solution of the compound of Example 1(a) (160 mg, 0.46 mmole) in trifluoroacetic acid (5 ml) was stirred at 23° for 20h. The solvent was thoroughly evaporated, and the residue vacuum dried to afford the title compound (220 mg, 100%). $^1H$ NMR (400 MHz, $CDCl_3$) δ8.78 (d, 1H), 7.29 (s, 2H), 4.90 (t, 1H), 2.90 (m, 1H).

c) (3R, 1'S)-N-benzyloxy-3-(N'-(1'-isopropyl-1'-imidazol-2-yl) methylaminocarbonyl)-5-methyl hexanamide A solution of the compound of Example 1b) (218 mg, 0.53 mmole), O -benzylhydroxylamine hydrochloride (85 mg, 0.53 mmole), $Et_3N$ (214 mg, 2.12 mmole) and benzotriazolo-1-yloxy-tris(dimethylamino)phosphonium hexafluorophosphate (234 mg, 0.53 mmole) in $CH_2Cl_2$ (50 ml) was stirred for 18 h. The solvent was removed, and the residue taken up in EtOAc (100 ml). The EtOAc was washed with $H_2O$, aq $Na_2CO_3$, dried ($K_2CO_3$), and the solvent evaporated. The residue was triturated with hot $Me_2CO$, cooled and filtered, and afforded the tire compound (92 mg, 44%). $^1H$ NMR (400 MHz, $CDCl_3$/DMSO—$D_6$) δ7.36 (m, 5H), 6.89 (s, 2H), 4.88 (t, 1H), 4.72 (d of d, 2H).

d) (3R, 1'S)—N-hydroxy-3-(N'-(1'-isopropyl-1'-imidazol-2-yl) methylaminocarbonyl)-5-methyl hexanamide To a solution of the compound of Example 1(c) (42 mg, 0.1 mmole) in EtOH (5 ml) was added 10% Pd/C (50 mg), and the mixture was hydrogenated at 1 atmosphere $H_2$ for 4 h. The catalyst was filtered, and the solvent evaporated. The residue was recrystallized from a mixture of MeOH and MeCN and afforded the title compound (18 mg, 55%). (400 MHz, DMSO—$D_6$) δ7.90 (d, 1H), 6.80 (s, 1H), 4.74 (t, 1H), 2.74 (m, 1H), 2.30 (d of d, 1H), 2.12 (d of d, 1H), 2.04 (m, 1H), 1.42 (m, 1H), 1.34 (m, 1H), 1.06 (m, 1H), 0.78 (m, 12H).

Example 2

Preparation of (2S, 3R, 1'S)—N-2-Dihydroxy-3-[(1'-isopropyl-1'-imidazol-2-yl)methylaminocarbonyl]-5-methyl hexanamide (wherein $R_1$=OH, $R_4$=i-propyl)

a) (1S)-1-t-butoxycarbonylamino-1-isopropyl-1-(imidazol-2-yl)methane

A solution of (1S)-1-(imidazol-2-yl)-2-methylpropylamine (330 mg, 2.37 mmole) and di-t-butylpyrocarbonate (1.04 g, 4.75 mmole) in MeOH (5ml) was stirred for 48 h. The reaction was diluted with MeOH (5ml), treated with 2.5N NaOH (2 ml), and stirred for 0.5 h. The reaction was diluted with $H_2O$ (20 ml), extracted with $Et_2O$, the extracts were washed with $H_2O$, dried ($MgSO_4$), and the solvent evaporated to afford the title compound (462 mg, 82%).

b) (1S)-1-t-butoxycarbonylamino-1-isopropyl-1-(1-benzyloxymethylimidazol-2-yl)methane A mixture of the compound from Example 2(a) (442 mg, 1.85 mmole), benzyl chloromethyl ether (318 mg, 2.03 mmole), and $Et_3N$ (205 mg, 2.03 mmole) in MeCN (5 ml) was heated at 70° for 18 h. The solvent was evaporated, the residue taken up in $H_2O$, and extracted with $Et_2O$. The extracts were washed with $H_2O$, dried ($MgSO_4$), and the solvent evaporated. The residiue was purified by flash chromatography (silica gel, 1% methanol/chloroform) and yielded the title compound (590 mg, 89%). $^1H$ NMR (400 MHz, $CDCl_3$) δ7.00 (s, 1H), 6.92 (s, 1H), 4.64 (t, 1H), 2.24 (m, 1H).

c) (1S)-1-(1-benzyloxymethylimidazol-2-yl)-2-methylpropylamine

A solution of the compound from Example 2(b) (590 mg, 1.64mmole) in a mixture of $CDCl_3$ (5 ml) and TFA (2 ml) was stirred at 23° for 4 h. The solvents were evaporated, and the residue was taken up in $H_2O$, basified, and extracted with $Et_2O$. The extracts were dried ($MgSO_4$), and the solvent evaporated to yield the title compound as an oil (380 mg, 89%). $^1H$ NMR (400 MHz, $CDCl_3$) δ6.98 (s, 1H), 6.90 (s, 1H), 3.74 (d, 1H), 2.12 (m, 1H).

d) 2-(S)-(2,2-dimethyl-5-oxo-1,3-dioxolan-4-(R)-yl)-4-methylpentanoic acid pentafluorophenyl ester A solution of 2-(S)-(2,2-dimethyl-5-oxo-1,3-dioxolan-4-(R)-yl)-4-methylpentanoic acid (1.1 g, 4.78 mmole), pentafluorophenol (970 mg, 5.27 mmole), and 1-dimethylaminopropyl-3-ethyl carbodiimide methiodide (1.42 g, 4.78 mmole) in $CH_2Cl_2$ (25 ml) was stirred at 23° for 24 h. The reaction was washed with $H_2O$, 5% aqueous $K_2CO_3$, $H_2O$, dried ($K_2CO_3$), and the solvent evaporated, to yield the title compound (1.39 g, 74%).

e) 2-(S)-(2,2-dimethyl-5-oxo-1,3-dioxolan-4-(R)-yl)-4-methylpentanoic acid, N-[2-methyl-1-(S)-(1-benzyloxymethylimidazol-2-yl)]propylamide A solution of the compound from Example 2(d) (1.0 g, 2.53 mmole), and the compound from Example 2(c) (654 mg, 2.53 mmole) in DMF (3 ml) was stirred for 24 h. The reaction was diluted with $H_2O$ (10 ml), basified ($K_2CO_3$), and extracted with $Et_2O$. The extracts were washed with $H_2O$, aqueous $K_2CO_3$, dried ($K_2CO_3$), and the solvent evaporated. The residue was purified by flash chromatography (silica gel, 1% methanol/chloroform) and yielded the titled product (620 mg, 52%). $^1H$ NMR (400 MHz, $CDCl_3$) δ7.00 (s, 1H), 6.91 (s, 1H), 4.96 (t, 1H), 1.54 (s, 3H), 1.50 (s, 3H).

f) (2S, 3R, 1'S)-2-hydroxy-3-[1'-isopropyl-1'-(1-benzyloxymethylimidazol-2-yl)methylaminocarbonyl]-5-methyl hexanoic acid A solution of the compound in Example 2(e) (420 mg, 0.89 mmole) in a mixture of ethylene glycol (2 ml), THF (2 ml), $H_2O$ (1 ml), and 3N HCl (1 ml), was stirred at 60° for 1 h. The reaction was cooled to 23° and treated with a solution of LiOH (200 mg) in $H_2O$ (5 ml), and stirred for 30 min. The solution was poured into a pH 5 buffer (50 ml), and extracted with EtOAc. The extracts were washed once with $H_2O$, dried ($MgSO_4$), and the solvent evaporated to yield the title product (364 mg, 95%). $^1H$ NMR (400 MHz, $CDCl_3$) δ7.18 (s, 1H), 6.96 (s, 1H), 4.92 (t, 1H), 4.54 (s, 2H), 4.20 (d, 1H).

g) (2S, 3R, '1S)-N-benzyloxy-2-hydroxy-3-[1'-isopropyl-1'-(1-benzyloxymethylimidazol-2-yl)methylaminocarbonyl]-5-methyl hexanamide The compound of Example 1(f) can be reacted with O-benzylhydroxylamine hydrochloride in the presence of $Et_3N$ and benzotriazolo-1-yloxy-tris(dimethylamino) phosphonium hexafluorophosphate in $CH_2Cl_2$ in a manner analogous to that of Example 1(c) to give the titled compound.

h) (2S, 3R, 1'S)-N,2-dihydroxy-3-[1'-isopropyl- 1'-(imidazol-2-yl)methylaminocarbonyl]-5-methyl hexanamide The compound of Example 1(g) can be deprotected by hydrogenating a solution of the compound in MeOH over a 10% Pd/C catalyst in an analogous manner to that of Example 1 (d), to give the titled compound.

Example 3

Preparation of (2S, 3R, 1'S)-N-2-Dihydroxy-3-[(1't-butyl-1'-imidazol-2-yl)methylaminocarbonyl]-5-methyl hexanamide (wherein $R_1$=oh, $R_4$=t-butyl)

a) N-carbobenzyloxy-t-leucine

A solution of tert-leucine (16.7 g, 0.13 mole) in a mixture of $H_2O$ (100 ml) and 2.5N NaOH (51 ml) was cooled to 0° and stirred rapidly. Solutions of benzyoxychloroformate (21.7 ml, 0.15 mole) in $Me_2CO$ (40 ml) and 2.5N NaOH (62 ml) were added portionwise and alternately, at such a rate that the temperature of the reaction did not exceed 5°. After the additions, the reaction was stirred at 0° for 2 h. The reaction was diluted with $H_2O$ (200 ml), and washed 3 times with $Et_2O$. The aqueous phase was acidified to pH 1, and extracted with $CH_2Cl_2$. The extracts were washed with $H_2O$, dried ($MgSO_4$), and the solvent evaporated to yield the title compound (28 g, 82%). $^1H$ NMR (400 MHz, $CDCl_3$) δ7.38 (m, 5H), 5.45 (d, 1H), 5.12 (d of d, 2H), 4.22 (d, 1H), 1.00 (s, 9H).

b) N-carbobenzyloxy-t-leucine, pentafluorophenyl ester

A solution of the compound from Example 3(a) (1.7 g, 6.4 mmole), pentafluorophenol (1.2 g, 6.52 mmole), and 1-(2-morpholinoethyl)-3-cyclohexyl carbodiimide metho-p-toluene sulfonate (2.71 g, 6.4 mmole) in $CH_2Cl_2$ (50 ml) was stirred at 23° for 3 days. The reaction was washed once with $H_2O$, and twice with aqueous $K_2CO_3$, dried ($K_2CO_3$), and the solvent removed, and yielded the title compound (2.02 g, 73%). $^1H$ NMR (400 MHz, $CDCl_3$) δ5.39 (d, 1H), 5.16 (s, 2H), 4.50 (d, 1H), 1.10 (s, 9H).

c) N-methoxy-N-methyl carbobenzyloxy-t-leucineamide

A solution of the compound from Example 3(b) (14.82 g, 0.034mole) and N,O-dimethylhydroxylamine hydrochloride (9.9 g, 0.1 mole) in DMF (200 ml) was treated with $Et_3N$ (14.25 ml, 0.1 mole) and stirred at 23° for 7 days. The reaction was diluted with $H_2O$ (300 ml), and extracted three times with $Et_2O$. The extracts were washed with $H_2O$, dried ($K_2CO_3$), and the solvent removed. Purification was acomplished by flash chromatrography (silica gel, 30% EtOAc/hexane, and afforded the title product (6.2 g, 59%. $^1H$ NMR (400 MHz, $CDCl_3$) δ5.10 (d of d, 2H), 4.70 (d, 1H), 3.80 (s, 3H), 3.22 (s, 3H), 0.98 (s, 9H).

d) carbobenzyloxy-t-leucinal

A solution of the compound from Example 3(c) (910 mg, 2.96 mmole) in THF (10 ml) was cooled to −50° and treated dropwise with a 1N solution of LAH in THF (3 ml). After 1 h, EtOAc (2 ml) was added, and the cooling bath removed. As the reaction warmed to 23°, $H_2O$ (0.12 ml), 2.5N NaOH (0.18 ml), and $H_2O$ (0.3 ml) was added, stirring continued 30 min, and the solids filtered. The filtrate was evaporated, and afforded the title compound (630 mg, 85%). $^1H$ NMR (400 MHz, $CDCl_3$) δ5 9.78 (s, 1H), 5.08 (s, 2H), 4.24 (d, 1H), 1.02 (s, 9H).

e) (1S)-N-carbobenzyloxy-1-(imidazol-2-yl)-2,2-dimethylpropyl amine

A solution of the compound of Example 3(d) (630 mg, 2.53 mmole) and glyoxal trimer dihydrate (312 mg, 1.27 mmole) in MeOH (4 ml) containing $NH_3$ (200 mg) was stirred at 23° for 24 h. The reaction was diluted with $H_2O$ (10 ml), and extracted with EtOAc. The extracts were washed with $H_2O$, dried ($MgSO_4$), and the solvents evaporated. The residue was purified by flash chromatography (silica gel, 3% MeOH/$CHCl_3$) to afford the title compound (380 mg, 52%). $^1H$ NMR (400 MHz, $CDCl_3$) δ6.90 (s, 2H), 5.10 (d, 1H), 5.00 (d, 1H), 4.68 (d, 1H).

f) 1-(imidazol-2-yl)-2,2-dimethylpropyl amine

A solution of the compound from Example 3(e) (380 mg, 1.32 mmole) in MeOH (10 ml) was treated with 10% Pc/C (100 mg) and hydrogenated under 1 atmosphere $H_2$ pressure for 48 h. The catalyst was filtered, and the filtrate evaporated to afford the title compound (200 mg, 100%).

g) 2-(S)-(2,2-dimethyl-5-oxo-1,3-dioxolan-4-(R)-yl)-4-methylpentanoic acid, N-[2,2-dimethyl-1-(S)-(imidazol-2-yl)]propylamide A solution of 2-(S)-(2,2-dimethyl-5-oxo- 1,3-dioxolan-4-(R)-yl)-4-methylpentanoic acid (346 mg, 1.5 mmole), hydroxybenzotriazole (300 mg), 1-cyclohexyl-3-(2-morpholinoethyl) carbodiimide metho-p-toluenesulfonate (635 mg, 1.5 mmole), and the compound from Example 3(f) (230 mg, 1.5 mmole) in $CH_2Cl_2$ (10 ml) was stirred at 23° for 48 h. The reaction was washed with aqueous $Na_2CO_3$, $H_2O$, dried ($MgSO_4$), and the solvent evaporated. The residue was purified by flash chromatography (silica gel, 3% MeOH/$CHCl_3$), and afforded the titled product (160 mg, 28%). $^1H$ NMR (400 MHz, $CDCl_3$) δ6.98 (s, 2H), 5.20 (d, 1H), 4.50 (d, 1H), 2.88 (m, 1H), 1.50 (s, 3H), 1.42 (s, 3H), 1.00 (s, 9H).

h) (2S, 3R, 1'S)-2-hydroxy-3-[2',2'-dimethyl-1'-(imidazol-2-yl)propylaminocarbonyl]-5-methyl hexanoic acid The compound of Example 3(g) can be reacted with HCl in a mixture of $H_2O$ and ethylene glycol in a manner analagous to that of Example 2(f) to give the titled compound.

i) (2S, 3R, 1'S)—N-benzyloxy-2-hydroxy-3-[2',2'-dimethyl-1'-(imidazol-2-yl)propylaminocarbonyl]-5-methyl hexanamide The compound of Example 3(h) can be reacted with O-benzylhydroxylamine hydrochloride in the presence of $Et_3N$ and benzotriazolo-1-yloxy-tris(dimethylamino) phosphonium hexafluorophosphate in $CH_2Cl_2$ in a manner analogous to that of Example 1(c) to give the titled compound.

j) (2S, 3R, 1'S)—N,2-dihydroxy-3-[2',2'-dimethyl- 1'-(imidazol-2-yl)propylaminocarbonyl]-5-methyl hexanamide The compound of Example 3(i) can be deprotected by hydrogenating a solution of the compound in MeOH over a 10% Pd/C catalyst in an analogous manner to that of Example 1(d), to afford the titled compound.

In an analogous manner to that of Example 1 or by the general synthetic methods indicated herein the following compounds may be prepared:

Example 4. N-hydroxy-3-N'-(1'-t-butyl-1'-imidazol-2-yl) methylaminocarbonyl-5-methyl hexanamide

METHODS OF TREATMENT

The compounds of Formula (I) or a pharmaceutically acceptable salt thereof can be used in the manufacture of a medicament for the prophylactic or therapeutic treatment of any disease state in a human, or other mammal, which is exacerbated or caused by a matrix-degrading metalloproteinases.

Compounds of formula (I) are capable of inhibiting metalloproteinases involved in tissue degradation, such as collagenase, stromelysin, gelatinase and collagenase (IV). The role of these metalloproteinases in well known in the art and management of these metalloproteinases would be useful to treat a wide variety of disease states and conditions thereof. Most notably, diseases involving tissue degradation which includes arthopathy, such as rheumatoid arthritis, osteoporosis, inflammatory disease, dermatological diseases, bone reasorption disease, inhibition of angiogenesis, regression of tumors and therefore in treatment of cancers caused thereby, and cornea/ulceration. Many patents have published or issued to these various diseases and while not inclusive, U.S. Pat. Nos. 4,996,358; 4,599,361; 5,240,958; WO 91/02716; EPO 498 665 A1; WO 90/05716; WO 90/05719; and WO 93/21942 are hereby incorporated by reference in their entirety. Similarly incorporated by reference herein is *Arthritis and Rheumatism*, 20, pg. 1231–1239 (1977) which provides evidence implicating collagenase as a key enzyme in the breakdown of articular cartilage and bone in rheumatoid arthritis. The inhibition of these metalloproteinases is of benefit in controlling, reducing and alleviating many of these disease states.

Accordingly, the present invention provides a method of treating a matrix-degrading metalloproteinase mediated disease which comprises administering an effective matrix-degrading inhibiting amount of a compound of formula (I) or a pharmaceutically acceptable salt thereof. In particular, the present invention is to a method of treating a collagenase mediated disease state or where collagenolytic activity is important.

In particular, compounds of formula (I) or a pharmaceutically acceptable salt thereof are of use in the prophylaxis or therapy of any disease state in a human, or other mammal, which is exacerbated by or caused by excessive or unregulated collagenolytic activity by such mammal's cell.

In order to use a compound of formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of formula (I) and a pharmaceutically acceptable carrier or diluent.

Compounds of formula (I), pharmaceutically acceptable salts thereof and pharmaceutical compositions incorporating such may conveniently be administered by any of the routes conventionally used for drug administration, for instance, orally, topically, parenterally or by inhalation. The compounds of formula (I) may be administered in conventional dosage forms prepared by combining a compound of formula (I) with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of formula (I) may be administered topically, that is by non-systemic administration. This includes the application of a compound of formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of formula (I), total daily dosage for oral administration will be from about 250 mg to about 5000 mg. A suitable daily dosage will be from about 0.1 mg/kg to about 300 mg/kg of total body weight, preferably from about 1 to 100 mg/kg.

The daily parenteral, in particular intra-articularly into the affected joint, will be from about 0.5 mg/kg to 100 mg/kg, resulting in a daily administration of about 1 mg to 5 grams of compound for a 70 kg mammal.

The daily topical dosage regimen will be similar to parenteral of 0.5 mg to 100 mg/kg and typically be in the range of 10 mg to 100 mg of compound. For administration to the eyes, 0.1 to 1 mg of compound per administration.

It will also be recognized by one of skill in the art that the optimal quantity and spacing of individual dosages of a compound of formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of formula (I) or a pharmaceutically acceptable salt thereof given per day for a defined number of days, can be ascertained by those skilled in the art using conventional course of treatment determination tests.

The invention will now be described by reference to the following examples which are merely illustrative and are not to be construed as a limitation of the scope of the present invention.

BIOLOGICAL EXAMPLES

The collagenase inhibitory activity of compounds of the present invention are determined by the in vitro assays as described by the procedure of Cawston and Barrett, Anal. Biochem. 99, 340–345 (1979), and as described in U.S. Pat. Nos. 5,240,598 or 4,599,361 whose disclosures are hereby incorporated by reference. The compound of Example 1 was found to be an effective inhibitor of collagenase activity.

The stromelysin inhibitory activity of the compounds of Formula (I) may be determined by the procedure of Cawston et al., Biochem. J., 195, 159–165 (1981), whose disclosure is hereby incorporated by reference.

Additional testing for anti-inflammatory and chondroprotective effects of the compounds of Formula (I) may also be done using the adjuvant arthritis (AA) rat model which is well known to those of skill in the art.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to the formula

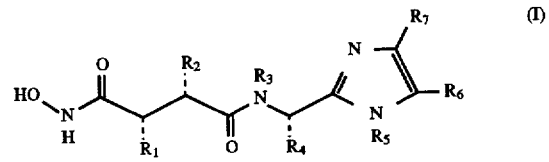

wherein $R_1$ is hydrogen, hydroxy, optionally substituted $C_{1-6}$ alkyl, optionally substituted $C_{1-6}$ alkenyl, phenyl, optionally substituted phenyl $C_{1-6}$ alkyl-, $R_7$—S(O)$_n C_{1-6}$-alkyl-;

n is 0 or an integer having a value of 1 or 2;

$R_7$ is $C_{1-6}$ alkyl, phenyl, phenyl $C_{1-6}$ alkyl, heterocyclic, heterocyclic $C_{1-6}$ alkyl, heteroaryl, heteroaryl $C_{1-6}$ alkyl, $C_{1-6}$ alkyl carbonyl, or phenacyl, all of which may be optionally substituted one to four time independently from C1–6 alkyl, $C_{1-6}$ alkoxy, hydroxy, thio $C_{1-6}$alkyl, amino, halogen, $CF_3$ or nitro;

$R_2$ is hydrogen, $C_{1-6}$alkyl, $C_{1-6}$ alkenyl, phenyl $C_{1-6}$ alkyl, cycloalkyl $C_{1-6}$ alkyl, or cycloalkenyl $C_{1-6}$ alkyl;

$R_3$ is hydrogen or methyl;

$R_4$ is hydrogen, $C_{1-6}$ alkyl, cyclopropyl, an amino acid residue, optionally substituted phenyl, optionally substituted phenyl $C_{1-6}$ alkyl-, optionally substituted —$C_{1-6}$-alkyl-oxy $C_{1-6}$alkyl, optionally substituted —$C_{1-6}$ alkyl oxy $C_{1-6}$ alkyl phenyl, or an optionally substituted —$C_{1-6}$ alkyl oxy phenyl;

wherein the phenyl or benzyl moiety is independently substituted one to four times by halogen, $C_{1-6}$ alkyl, $C_{1-6}$ alkoxy, hydroxy, thiol, $C_{1-6}$alkylthio-, —$NR_{12}R_{13}$, —$NHR^a$, —$NO_2$, —$C(O)_2R_{14}$, —$C(O)_2NR_{12}R_{13}$, cyanoamino, $R_{14}C(O)$—O—, $C_{1-6}$ alkyl OH, $C_{1-6}$ alkyl-$C(O)_2R_{14}$, $C_{1-6}$ alkyl-oxy-$C_{1-6}$ alkyl, $C(O)C_{1-6}$ alkyl$NR_{12}R_{13}$, or $C_{1-6}$ alkyl-$(O)_2C$—$R_{14}$;

$R^a$ is hydrogen, $C_{1-6}$ alkyl, or the side chain of an amino acid, $R_{14}$ is hydrogen, $C_{1-6}$ alkyl, $C_{3-7}$ cycloalkyl, $C_{3-7}$ cycloalkyl $C_{1-6}$ alkyl, aryl $C_{1-6}$ alkyl, heteroaryl$C_{1-6}$alkyl, or heterocyclic $C_{1-6}$ alkyl;

$R_5$ is hydrogen or $C_{1-6}$ alkyl;

$R_6$ and $R_7$ are independently hydrogen, halogen, $CF_3$, $C_{1-6}$ alkyl, aryl, aryl$C_{1-6}$alkyl, heteroaryl, heteroaryl$C_{1-6}$alkyl, heterocyclic, heterocyclic $C_{1-6}$ alkyl, $(CHR_8)m'$ OH, $(CHR_8)m$ $C(O)_2R_{10}$, $(CHR_8)m$ $C(OH)(R_9)_2$, $(CR_8R_9)$-OH, $C(O)R_{11}$, $C(O)NR_{12}R_{13}$, $C(O)_2R_{10}$, or $NO_2$; or $R_6$ and $R_7$ can together form a fused C 2–4 alkylene, aryl or heteroaryl moiety;

m is 0 or an integer having a value of 1 or 2;

m' is an integer having a value of 1, 2, or 3;

$R_8$ and $R_9$ are independently hydrogen, $C_{1-4}$ alkyl or phenyl;

$R_{10}$ is hydrogen, $C_{1-6}$ alkyl, $C_{3-7}$ cycloalkyl, $C_{3-7}$ cycloalkyl $C_{1-}$alkyl, $C_{5-7}$ cycloalkenyl, aryl$C_{1-6}$alkyl, heteroaryl$C_{1-6}$alkyl, heterocyclic, heterocyclic $C_{1-6}$ alkyl all of which may be optionally substituted by halogen, hydroxyl, —$C_{1-6}$alkoxy, -thio$C_{1-6}$ alkyl, or $CF_3$;

$R_{11}$ is hydrogen, $C_{1-6}$ alkyl, $C_{3-7}$ cycloalkyl, $C_{3-7}$ cycloalkyl $C_{1-6}$ alkyl, $C_{5-7}$ cycloalkenyl, aryl, aryl$C_{1-6}$alkyl, heteroaryl, heteroaryl$C_{1-6}$ alkyl, heterocyclic, heterocyclic $C_{1-6}$ alkyl all of which may be optionally substituted by halogen, hydroxyl, —$C_{1-6}$ alkoxy, -thio$C_{1-6}$ alkyl, or $CF_3$;

$R_{12}$ and $R_{13}$ are independently hydrogen, $C_{1-6}$ alkyl, $C_{3-7}$ cycloalkyl, $C_{3-7}$ cycloalkyl $C_{1-6}$ alkyl, aryl, aryl$C_{1-6}$ alkyl, heteroaryl, heteroaryl $C_{1-6}$ alkyl, heterocyclic, heterocyclic $C_{1-6}$ alkyl or $R_{12}$ and $R_{13}$ may together with the nitrogen to which they are attached form a 5 to 7 membered ring which may additionally contain another heteroatom selected from O/N/or S;

or a pharmaceutically acceptable salt thereof.

2. The compound according to claim 1 wherein $R_1$ is hydrogen or hydroxy.

3. The compound according to claim 1 wherein $R_2$ is $C_{1-6}$ alkyl.

4. The compound according to claim 1 wherein $R_3$ is hydrogen.

5. The compound according to claim 1 wherein $R_4$ is hydrogen, $C_{1-6}$ alkyl, cyclopropyl, an amino acid residue, optionally substituted phenyl, optionally substituted phenyl $C_{1-6}$ alkyl-, optionally substituted(phenyl) —$C_{1-6}$-alkyl-oxy $C_{1-6}$alkyl, optionally substituted —$C_{1-6}$ alkyl oxy$C_{1-6}$ alkyl phenyl, or an optionally substituted —$C_{1-6}$ alkyl oxy phenyl;

wherein the phenyl or benzyl moiety is independently substituted one to four times by halogen, $C_{1-6}$ alkyl, $C_{1-6}$ alkoxy, hydroxy, thiol, $C_{1-6}$alkylthio-, —$NR_{12}R_{13}$, —$NHR^a$, —$NO_2$, —$C(O)_2R_{14}$, —$C(O)_2NR_{12}R_{13}$, cyanoamino, $R_{14}C(O)$—O—, $C_{1-6}$ alkyl OH, $C_{1-6}$alkyl-$C(O)_2R_{14}$, $C_{1-6}$alkyl-oxy-$C_{1-6}$alkyl, $C(O)C_{1-6}$ alkylN$R_{12}R_{13}$, or $C_{1-6}$alkyl-$(O)_2C$—$R_{14}$.

6. The compound according to claim 1 wherein $R_6$ and $R_7$ are independently hydrogen, bromine, chlorine, $CF_3$, $C_{1-6}$ alkyl, phenyl, $(CHR_8)$m'OH, $(CHR_8)$m $C(O)_2R_{10}$, $(CHR_8)$m $C(OH)(R_9)_2$, $(CR_8R_9)$—OH, $C(O)R_{11}$, $C(O)NR_{12}R_{13}$, $C(O)_2R_{10}$, or $NO_2$; or $R_6$ and $R_7$ can together form a fused C 2-4 alkylene, aryl or heteroaryl moiety;

$R_{10}$ is hydrogen, or $C_{1-6}$ alkyl; and $R_{11}$ is hydrogen, $C_{1-6}$ alkyl, or phenyl.

7. The compound according to claim 6 wherein $R_6$ and $R_7$ together form a fused aryl ring.

8. The compound according to claim 6 wherein $R_1$ is hydrogen or hydroxy; $R_2$ is $C_{1-6}$ alkyl and $R_3$ is hydrogen.

9. The compound according to claim 1 wherein one of $R_6$ and $R_7$ are hydrogen, $C_{1-6}$ alkyl, $C_{3-6}$ cycloalkyl, phenyl, benzyl, $CF_3$, bromine, $C(O)_2CH_3$, $C(O)H$, $CH_2OH$, $CH(OH)CH_3$, $CH(OH)$isopropyl, $CH(OH)$phenyl, $NO_2$, $C(O)NH_2$, $(CH_2)_2C(O)_2CH_3$, or both of $R_6$ and $R_7$ are methyl, dibromo or together form a fused aryl ring with the imidazole.

10. The compound according to claim 1 wherein $R_4$ is hydrogen, methyl, t-butyl, ethyl, propyl, isobutyl, cyclopropyl or benzyl.

11. A pharmaceutical composition comprising a pharmaceutically acceptable carrier or diluent and a compound according to claim 1.

12. A method of treating a matrix degrading metalloproteinase mediated disease in an animal in need thereof which method comprises administering to said animal an effective matrix degrading metalloproteinase mount of a compound according to claim 1.

13. The method according to claim 12 wherein the matrix degrading metalloproteinase is collagenase.

14. The method according to claim 12 wherein the matrix degrading metalloproteinase mediated disease is arthritis, osteoporosis, or a bone reasorption disease.

15. A method of treating inflammation in an animal in need thereof which method comprises administering to said animal an effective amount of a compound according to claim 1.

16. A method of treating arthritis in an animal in need thereof which method comprises administering to said animal an effective amount of a compound according to claim 1.

* * * * *